(12) United States Patent
Kruse et al.

(10) Patent No.: US 9,255,904 B2
(45) Date of Patent: Feb. 9, 2016

(54) STEP-CHANGE SENSOR FOR PUMPED AND UNPUMPED OPERATION

(71) Applicants: Peer Kruse, Bietigheim-Bissingen (DE); Jens Schneider, Leonberg (DE); Lothar Diehl, Gerlingen (DE); Gerhard Schneider, Pettstadt (DE); Christoph Peters, Stuttgart (DE)

(72) Inventors: Peer Kruse, Bietigheim-Bissingen (DE); Jens Schneider, Leonberg (DE); Lothar Diehl, Gerlingen (DE); Gerhard Schneider, Pettstadt (DE); Christoph Peters, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 583 days.

(21) Appl. No.: 13/654,106

(22) Filed: Oct. 17, 2012

(65) Prior Publication Data
US 2013/0092559 A1  Apr. 18, 2013

(30) Foreign Application Priority Data
Oct. 17, 2011  (DE) .......................... 10 2011 084 653

(51) Int. Cl.
*G01N 27/407* (2006.01)

(52) U.S. Cl.
CPC .......... *G01N 27/4072* (2013.01); *G01N 27/407* (2013.01)

(58) Field of Classification Search
CPC .......... F01N 2560/02; F01N 2560/025; F01N 2560/026; G01N 27/4071; G01N 27/409; G01N 27/41; G01N 27/4072
See application file for complete search history.

(56) References Cited

U.S. PATENT DOCUMENTS

| 5,496,461 | A | 3/1996 | Hötzel et al. |
| 2003/0121800 | A1 * | 7/2003 | Wahl et al. ................. 205/780.5 |

FOREIGN PATENT DOCUMENTS

| DE | 43 33 230 | 4/1995 |
| DE | 199 63 566 | 7/2001 |
| DE | 100 43 089 | 3/2002 |
| DE | 100 51 833 | 5/2002 |
| DE | 10 2010 039 392 | 2/2012 |
| JP | 2010249795 A * | 11/2010 ........... G01N 27/416 |

OTHER PUBLICATIONS

JPO computer-generated English language translation of Mizutani et al. JP 2010-249795 A, patent published Nov. 4, 2010, translation downloaded Apr. 13, 2015.*
Robert Bosch GmbH, "Sensoren im Kraftfahrzeug," 1st Edition, pp. 160-165, 2010; and English translation of pp. 160 and 164.

* cited by examiner

*Primary Examiner* — Alexander Noguerola
(74) *Attorney, Agent, or Firm* — Kenyon & Kenyon LLP

(57) ABSTRACT

A sensor device for sensing at least a proportion of at least one gas component of a gas in a measurement gas space, in particular for detecting oxygen in an exhaust gas of a combustion machine, is proposed. The sensor device includes at least one sensor element. The sensor element includes at least one first electrode and at least one first reference electrode and at least one second reference electrode. The second reference electrode is connected to at least one reference gas channel. The first electrode is connected to the first reference electrode and the second reference electrode by at least one respective solid electrolyte. The sensor element has at least one diffusion element between the first reference electrode and the reference gas channel.

12 Claims, 3 Drawing Sheets

STEP-CHANGE SENSOR FOR PUMPED AND UNPUMPED OPERATION

CROSS REFERENCE

The present application claims the benefit under 35 U.S.C. §119 of German Patent Application No. DE 102011084653.0 filed on Oct. 17, 2011, which is expressly incorporated herein by reference in its entirety.

BACKGROUND INFORMATION

Sensor elements for sensing at least a proportion of at least one gas component of a gas in a measurement gas space are described in, for example, Robert Bosch GmbH: "Sensoren im Kraftfahrzeug, 1. Auflage 2010" ["Sensors in motor vehicles, 1st edition 2010"], pages 160-165. The sensor devices may, in particular, be lambda probes. Lambda probes based on an ionically conductive sensor element, typically made of zirconium dioxide ($ZrO_2$), generally compare an electrochemical potential of an electrode on the measurement gas side with an electrochemical potential of a reference electrode. The reference electrode is preferably situated in a defined reference gas, typically air. A measured variable collected for the sensing operation may usually be, for example, a Nernst voltage which develops between the two electrodes, the Nernst voltage generally being the greater, the greater is, in particular, a partial pressure difference, for example of oxygen ($O2$), between the two electrodes.

German Patent Application No. DE 100 43 089 A1 describes, for example, a sensor for determining gas components and/or concentrations of gas constituents in gas mixtures, the sensor having a reference electrode which may be exposed, via a reference gas channel, to a reference gas, in particular air or an oxygen-containing gas. In one advantageous embodiment, there is provided beside the reference gas channel from the internal volume of the sensor structure to the reference electrode a further gas channel, in particular having a catalytically active region or a catalytically active surface. The further gas channel may, for example, be configured as a double reference channel that is capable of taking on, for example, the reaction of hydrocarbons (HC).

Signal accuracy may be increased, for example, by an open reference channel, in particular of a small cross-section, as described, for example, in German Patent Application No. DE 10 2010 039 392.

German Patent No. DE 100 51 833 A1 describes a planar gas sensor element for the determination of gas components, wherein, in particular, electrodes at different temperature levels and on the reference side may be shifted. The reference electrode is in the form of a plurality of partial surfaces connected to one another in an electrically conductive manner. Owing to the division into a plurality of partial surfaces, the reference electrode, which, in particular, is of a large surface area, is not heated uniformly throughout, so that there are always hot spots and cold spots over the surface of the reference electrode, which distinctly reduces the effect of an exhaust gas temperature, the exhaust gas flow and the heating power of a heating element on a Nernst voltage produced. According to that patent, it is said to be advantageous if division of the reference electrode into a plurality of partial surfaces connected to one another in an electrically conductive manner is performed in such a way that those partial surfaces of the reference electrode that are at least to a large extent in a hot region have at least approximately the same internal resistance as those partial surfaces that are at least to a large extent outside the hot region.

In the case of conventional sensor devices, especially in the case of lambda probes, non-combusted hydrocarbons may be present, in particular in the reference gas channel, which usually consume a proportion of the oxygen supplied to the reference electrode, with the result that the oxygen concentration at the reference electrode may be reduced, thereby interfering with probe function. That behavior is also known as CSD (characteristic shift down, also referred to as continuous shift down or chemical shift down). Furthermore, non-combusted hydrocarbons may preferably be oxidized over hot, catalytically active surfaces, especially at the reference electrode.

To avoid contamination of the reference air by rich gases, in particular CSD, generally two concepts are pursued in the related art:

On the one hand, in the case of a reference air channel, an artificial reference may be produced by a reference pump current, for example as described in German Patent Nos. DE 199 63 566 A1 and DE 43 33 230 A1. Preferably, the reference electrode may be exposed to the artificial reference, which may be produced, for example, by a reference pump current from an outer electrode to the reference electrode. The reference pump current may be obtained, for example, by suitable connection of the sensor device, especially a probe, in a control device. For this mode of operation, the probe design should have as a rule an impermeable reference channel, for example a reference air channel with a high diffusion resistance, for example one that is narrow and/or has a low porosity, for example in order that oxygen, which, in particular, may be pumped to the reference electrode especially by the reference pump current, stays at the reference electrode and/or in order that as little rich gas as possible is able to reach the reference electrode, while a reference gas channel should preferably be formed with a more large-pored material so that bursting of the sensor element, for example due to an oxygen overpressure at the reference electrode, is preferably prevented. That form of implementation is generally also referred to as a "pumped reference".

In a further form of implementation, an open and/or very porous reference air channel is generally used, such a form of implementation generally being termed an "air reference", and the reference electrode is preferably exposed directly to ambient air. This makes it possible, for example, for the hydrocarbons to be reacted to exhaustion by oxygen that is able to reach the reference electrode through the open and/or very porous reference air channel. Preferably, no reference pump current is impressed from the outer electrode to the reference electrode. The reference air channel preferably has a low diffusion resistance, for example by virtue of being a wide reference air channel, preferably with a high porosity.

A particular disadvantage is that, depending on the mode of operation, in particular pumped reference or air reference, two different designs and/or types of probe are usually necessary.

It would therefore be desirable to have a sensor device, in particular a lambda probe, for example a $\lambda=1$-probe, capable of being operated selectively with a pumped reference or with an open reference, in particular with an air reference. In that way it is also possible, for example, for the number of control devices that are compatible with the sensor device, in particular the probe, to rise significantly.

SUMMARY

Accordingly, an example sensor device for sensing at least a proportion of at least one gas component of a gas in a measurement gas space and an example method for operating the sensor device are proposed, which to a great extent avoid and/or mitigate the disadvantages to be expected in conventional sensor devices and method.

The gas component may in principle be any gas, and preferably the gas component may be oxygen. The proportion may be, for example, a percentage and/or a partial pressure, in particular an oxygen percentage and/or an oxygen partial pressure. The gas may in principle be any gas, and in particular the gas may be an exhaust gas, for example with combustion residues, of a combustion engine. The measurement gas space may in principle be any space that may be filled with gas. Preferably, the measurement gas space may be an exhaust system of a combustion engine. The sensor device may, in particular, be a sensor device for detecting oxygen in an exhaust gas of a combustion machine, in particular a combustion engine. The combustion machine and/or the combustion engine may in principle be any machine capable of being powered by combustion reactions; in particular, it may be a motor vehicle, preferably an automobile.

The example sensor device may include at least one sensor element. A sensor element may, in particular, be a sensor device component that may be configured to deduce the proportion of the gas component through electrochemical processes, in particular, for example, in combination with a total pressure. The example sensor element may preferably be a lambda probe.

The example sensor element may include at least one first electrode and at least one first reference electrode and at least one second reference electrode. The first electrode and/or the first reference electrode and/or the second reference electrode may each be, in particular, an electrode. An electrode may be a component that may be acted upon by a voltage and/or an electric current. The first electrode may be, for example, an outer pumping electrode. The first reference electrode and/or the second reference electrode are preferably reference electrodes. A reference electrode may be, in particular, an electrode that is connected to a reference gas, for example air; the reference electrode may preferably be an electrode with which it is possible to measure an electrochemical potential of the reference gas, for example air.

The second reference electrode and optionally also the first reference electrode are connected to at least one reference gas channel, for example a reference channel and/or a reference air channel. The reference air channel may be, for example, a reference gas space. A reference gas channel and/or a reference gas space may in principle be a space that is constructed to be separate from the measurement gas space and/or that may be shielded off preferably in a gas-tight manner from the measurement gas space. Accordingly, preferably at least for the time periods relevant for a measurement, for example for several seconds, especially several minutes, gas from the measurement gas space is not able to reach the reference gas space directly. The first reference electrode may be connected to the same reference gas channel as the second reference electrode, but may also be connected to a different reference gas channel, for example to at least one second reference gas channel. A connection between the reference gas channel and the first reference electrode and/or the second reference electrode may be understood as being, for example, a direct connection and/or an indirect connection, for example via a diffusion layer. By way of the connection, an exchange of the gas components and/or of oxygen may be possible. The first reference electrode may also be separated from the second reference electrode and optionally also from the reference gas channel in a form such that preferably no gas exchange is possible.

The expressions "first" and/or "second" serve merely for identification and do not give an indication of any order and/or do not give an indication of whether the sensor device may not include further reference electrodes and/or reference gas channels and/or electrodes. For example, the sensor device may include a third reference electrode and/or further electrodes, for example a second electrode, in particular an inner pumping electrode.

The first electrode is connected to the first reference electrode and the second reference electrode via at least one respective solid electrolyte. For example, the first electrode may be connected to the first reference electrode via a first solid electrolyte and/or the first electrode may be connected to the second reference electrode via a second solid electrolyte. The first solid electrolyte and the second solid electrolyte may be of differing configurations and/or may be different solid electrolytes. Alternatively, the first solid electrolyte and the second solid electrolyte may, however, also be completely or partially identical components. The solid electrolyte may fundamentally be any ion-conducting solid body, preferably a solid body that is ion-conducting at least at and above a working temperature. For example, it may be an oxygen-ion-conducting solid body. Such solid bodies, in particular ceramic solid bodies, are fundamentally conventional. For example, it is possible to use yttrium-stabilized zirconium dioxide (YSZ) and/or other solid electrolytes, for example based on zirconium dioxide, for example scandium-doped zirconium dioxide (ScSZ). The solid electrolyte may, for example, include one or more solid electrolyte films and/or solid electrolyte pastes, which preferably may be hardened.

The sensor element further has at least one diffusion element, which is connected to the first electrode. A diffusion element may generally be understood as being an element configured to absorb gas and to enable the transport of gas by diffusion. In particular, the diffusion element may have at least one porous material, for example at least one porous layer. The diffusion element may be constructed to be separate from the first reference electrode, for example as a separate element. Alternatively or in addition, the diffusion element may, however, also be completely or partially integrated in the first reference electrode, for example by the reference electrode being completely or partially in the form of a porous electrode having at least one porous electrode material that is also capable of acting as a diffusion element and preferably as a gas accumulator. The diffusion element may generally be configured in particular as a gas accumulator. The connection between the diffusion element and the first reference electrode may in particular be such that a direct gas exchange is possible between the first reference electrode and the diffusion element. In particular, the diffusion element may directly adjoin the first reference electrode, for example as a porous layer lying directly on the first reference electrode. Other configurations are, however, also possible.

In one possible configuration, the at least one diffusion element may, for example, be formed completely or partially between the first reference electrode and the reference gas channel. In that case, a gas exchange between the diffusion element and the reference gas channel may be made possible. Alternatively or in addition, the diffusion element may also be completely or partially sealed with respect to the reference gas channel, for example by a gas-tight covering, so that a gas exchange between the diffusion element and the reference gas channel is prevented or at least made more difficult.

The diffusion element may, for example, be an element, in particular a film and/or a paste, that is capable of exhibiting diffusion properties, for example a capacity to diffuse oxygen. The diffusion element may preferably involve at least one diffusion layer. The diffusion layer may, however, also be constructed to be completely or at least partially separate from the diffusion element: for example, the diffusion element and the diffusion layer may at least partially overlap. The expression "between" may be understood here as referring, in particular, to an arrangement of the diffusion element in relation to the first reference electrode and the reference gas channel in which the diffusion element at least partially covers the first reference electrode, the diffusion element covering, in particular, at least a portion of a surface of the first reference electrode, which surface is toward the reference gas channel.

As stated above, the first reference electrode also may, in particular, be connected to the reference gas channel. In particular, a gas exchange between the first reference electrode and the reference gas channel may be made possible by the diffusion element. In one possible configuration, the diffusion element may, in particular, as already mentioned above, be disposed at least partially between the first reference electrode and the reference gas channel. By virtue of the diffusion element, in particular a gas exchange, for example an exchange of gases, for example air and/or oxygen and/or hydrocarbons, may be possible between the first reference electrode and the reference gas channel, in particular at least partially through the diffusion element. Preferably, the gas exchange between the first reference electrode and the reference gas channel is possible exclusively through the diffusion layer. A gas exchange may be understood as being an exchange of gas, especially in both directions, for example from the first reference electrode to the reference gas channel and from the reference gas channel to the first reference electrode. The gas exchange may preferably involve a diffusion, in particular a diffusion of oxygen. The diffusion layer may, in particular, be configured to prevent a diffusion of rich gas from the reference gas channel to the reference electrode and/or to promote a diffusion of oxygen between the reference electrode and the reference gas channel, for example from the reference electrode to the reference gas channel. The diffusion layer may preferably be of a configuration such that no excessively high oxygen overpressure forms, in particular such that no overpressure capable of leading to bursting of the sensor element, in particular the lambda probe, is able to develop.

In principle, the first reference electrode and/or the diffusion element may, however, also be completely or partially sealed with respect to the reference gas channel so that no direct gas exchange is made possible. In particular, the first reference electrode may be sealed with respect to the reference gas channel, a direct gas exchange between the first reference electrode and the reference gas channel being prevented. However, by way of an ion transport to the second reference electrode, for example a transport of oxygen ions, an indirect gas exchange between the first reference electrode and the reference gas channel may still be made possible, that is, a gas exchange involving a temporary conversion into ions.

For example, the sensor element may have, between the first reference electrode and optionally the diffusion element on the one hand and the reference gas channel on the other hand, at least one gas-tight covering, for example by at least one gas-tight cover element. The covering may, for example, have a non-porous layer by which a gas exchange is prevented. An overpressure, in particular an oxygen overpressure, at the first reference electrode may optionally be reduced by a conduction of ions, in particular a conduction of oxygen ions, to the second reference electrode, for example with subsequent oxidation. That conduction of ions may, for example, be a compensating current. The compensating current may usually be determined by the difference of the partial pressures, for example the oxygen partial pressures, at the first reference electrode and the second reference electrode and by the internal resistance between the two reference electrodes, in particular the internal resistance between the first reference electrode and the second reference electrode.

The sensor element may have a first internal resistance between the first electrode and the first reference electrode. The internal resistance may, in particular, be an internal resistance to ionic conduction, for example through the solid electrolyte, especially at a typical operating temperature, for example in a range from 500° C. to 1100° C. For example, the internal resistance may be an ohmic resistance to ionic conduction.

The sensor element may have a second internal resistance between the first electrode and the second reference electrode. The first internal resistance is preferably smaller than the second internal resistance. The first internal resistance may, for example, be smaller than the second internal resistance by a factor of 0.5, preferably a factor of 0.1, especially by a factor of 0.01.

An electrochemical performance of the first reference electrode may preferably be higher than an electrochemical performance of the second reference electrode. The electrochemical performance of an electrode may be understood as being the capacity for oxygen reduction and/or oxidation. The electrochemical performance usually correlates with the inverse internal resistance of the electrode.

The first reference electrode and the second reference electrode may preferably be electrically short-circuited. The first reference electrode and the second reference electrode may, in particular, have a common supply line, in particular a common voltage supply line. For example, the first reference electrode may also be connected to the second reference electrode, for example by an electrical conductor. The expression "short-circuited" may, in particular, be understood as meaning an ohmic resistance of less than $10\Omega$, for example of less than $1\Omega$, preferably of less than $0.1\Omega$. The expression "short-circuited" may, in particular, be understood as meaning that the first reference electrode and the second reference electrode have an identical electrical potential at any potential reference point.

The first reference electrode may be formed by at least one first region of an electrode disposed in the reference gas channel. A region of an electrode may, in particular, be a proportion of the electrode. The electrode disposed in the reference gas channel may, in particular, be an electrode that is at least partially connected to the reference gas channel. The second reference electrode may be formed by at least one second region of the electrode disposed in the reference gas channel. The expressions "first" and "second" serve merely for identification and give no indication of any order and no indication of whether the electrode has still further regions. The electrode disposed in the reference gas channel may, for example, also have further regions, for example at least one third region, which may or may not be assigned, for example, to the first reference electrode and/or to the second reference electrode and/or to a further reference electrode.

The first region and the second region may preferably be different. The first region may preferably be covered toward the reference gas channel by at least one diffusion layer. The diffusion layer may form at least a part of the diffusion element. A diffusion layer may be understood as being a layer and/or a film capable of exhibiting diffusion properties. For example, the diffusion layer may promote a diffusion of oxygen from the first region to the reference gas channel and/or to the diffusion element and/or may prevent a diffusion of hydrocarbons and/or rich gas from the reference channel to the first region.

As stated above, the first reference electrode and optionally also the diffusion element on the one hand and the reference gas channel on the other hand may also be shielded from one another in a gas-tight manner, for example by at least one gas-tight covering which may be disposed between the first reference electrode and optionally the diffusion element on the one hand and the reference gas channel on the other hand. In that manner or in a different manner it is possible, for example, to suppress a gas exchange to the first reference electrode.

The reference gas channel may preferably be of an open configuration. A reference gas channel may, for example, be of an open configuration if it is preferably filled with air, in particular exclusively with air. The reference air channel may, however, also be completely, and preferably partially, filled with a porous medium that renders possible a passage of gas and/or a diffusion of gas.

For example, the first reference electrode may be short-circuited with the second reference electrode by virtue of the fact that the reference gas channel may be at least partially or completely, preferably partially, filled with a gas-permeable, electrically conductive electrode material. The reference gas channel may in that case be in the form of a closed reference gas space. It is especially preferred, however, if the reference gas channel, for example in the form of a reference air channel, is connected to an ambient environment of the sensor element, for example an ambient environment of the engine space and/or the ambient air, so that an air exchange may be possible between that ambient environment and the reference gas space.

The sensor device may include at least one drive. The drive may be centralized or decentralized and may, for example, be completely or partially accommodated in an engine control unit of a motor vehicle. The drive may, however, also be completely or partially integrated in the sensor element. The drive may, for example, also be connected to the sensor element via an interface. The drive may, however, also be completely or partially integrated in other components, for example a plug. The drive may, for example, include at least one application device in order to apply electric current and/or voltage to the electrodes, in particular the first electrode and/or the first reference electrode and/or the second reference electrode and/or the electrode disposed in the reference gas channel and/or at least one other electrode. The application device may, for example, be a voltage source and/or a current source. The drive may further include, where applicable, a measuring device, for example a voltage-measuring device and/or a current-measuring device. The voltage-measuring device may, in particular, be configured to measure a Nernst voltage and/or a pump voltage and/or at least one other voltage. The current-measuring device may, in particular, be configured to measure a pump current and/or at least one other electric current. Furthermore, the drive may optionally include, for example, an evaluation device, for example a data-processing device. Further optionally, the drive may include at least one signal generator. The drive may optionally include, in addition, at least one closed-loop controller, for example at least one lock-in controller.

The drive may preferably be configured in a first operating mode to apply to the sensor element at least one pump voltage and/or at least one pump current between the first electrode and the first reference electrode. The first operating mode may, in particular, be an operating mode with a pumped reference. The drive may further be configured in a second operating mode to operate the sensor element without pump voltage and/or without pump current between the first electrode and the first reference electrode. The second operating mode may, in particular, be an operating mode with an air reference. The expressions "first" and "second" are used here merely for identification and give no indication of any order and no information as to whether more operating modes may be applied by the drive. In principle, there may, for example, be further operating modes. The first operating mode and/or the second operating mode may in principle be carried out in any order, in particular in a defined order, for example in an order that is programmed in the drive. The first operating mode and the second operating mode may, in particular, be used in alternating sequence. The drive may further be configured in the first operating mode and/or in the second operating mode to deduce the proportion of the gas component, in particular an oxygen partial pressure, by sensing of a voltage and/or an electric current between the first electrode and the first reference electrode and/or between the first electrode and the second reference electrode and/or between at least one electrical supply line of the first electrode and at least one electrical supply line of the first reference electrode and/or of the second reference electrode, for example by using a characteristic curve. The characteristic curve may, in particular, involve a relationship, especially a linear relationship, between the pump current between the first reference electrode and/or the second reference electrode and the first electrode, in particular the outer pumping electrode, and the proportion of the gas component, in particular when the total pressure is known, and/or the oxygen partial pressure.

A geometry of the first reference electrode may, for example, differ from a geometry of the second reference electrode. The geometry of the first reference electrode and/or of the second reference electrode may be understood as meaning, for example, an external shape and/or a topography of the first reference electrode and/or of the second reference electrode. For example, the first reference electrode and the second reference electrode may be constructed to be of differing sizes, for example with differing volumes and/or with surfaces of differing sizes.

The second reference electrode may, for example, be of a ring-form configuration. The ring-form shape may be a ring, in particular a circular shape with an internal opening which preferably also has a circular shape; in principle, the ring may be a completely closed ring or a ring that is an at least partially open ring, for example with multiple openings. The ring-form configuration does not necessarily have to be circular: for example, the ring may also be configured in the form of a polygon and/or a rectangle and/or a non-circular round form, for example an ellipse, in each case with or without at least one hole and/or at least one aperture which, for example, may also be of a ring-shaped and/or polygonal and/or rectangular and/or non-circular round and/or elliptical configuration. The first reference electrode may, for example, be in particular of a ring-shaped and/or polygonal and/or rectangular and/or non-circular round and/or elliptical configuration, preferably without a hole and/or without an aperture. Other configurations of the first reference electrode and/or of the second reference electrode are possible in principle.

The second reference electrode may surround the first reference electrode preferably in a ring shape. For example, the first reference electrode and the second reference electrode may overlap, it being possible for the first reference electrode and the second reference electrode to be disposed in different layers which may be oriented, for example, in substantially parallel relationship to each other. The sensor element may, in particular, be fabricated as a layered structure. The expression "surround" may be understood here as meaning a surrounding of the second reference electrode in relation to the first reference electrode, in particular a surrounding of the first reference electrode by a projection of the second reference electrode in one plane and/or layer of the former. The second reference electrode may surround the first reference electrode completely and/or at least partially.

An average temperature of the first reference electrode may preferably be higher than an average temperature of the second reference electrode. The average temperature of the first reference electrode and/or the average temperature of the second reference electrode may, in particular, be adjusted and/or regulated by at least one heating element. The heating element may, in particular, be encompassed by the sensor element. The heating element may, in particular, be configured to adjust and/or to regulate and/or to model the average temperature of the first reference electrode and/or the average temperature of the second reference electrode. For example, the average temperature of the first reference electrode and/or the average temperature of the second reference electrode may be increased and/or decreased, especially in stages. The heating element may, for example, be positioned closer to the first reference electrode than to the second reference electrode, in particular to obtain the temperature difference. The first reference electrode may preferably be disposed at least partially in at least one hot spot. A hot spot may preferably be a portion of the sensor element that has a higher temperature and/or a higher average temperature than the remainder of the sensor element. The second reference electrode may preferably be disposed outside of the hot spot. The hot spot may, in particular, be heated by the heating element. Preferably, the hot spot is situated in a region that includes the first electrode and/or the first reference electrode and/or at least a portion of the solid electrolyte, in particular a region of the solid electrolyte between the first electrode and the first reference electrode. The second reference electrode and/or a region of the solid electrolyte between the first electrode and the second reference electrode are preferably situated outside of the hot spot. For example, the sensor element and/or the sensor device may also include a plurality of heating elements, for example one heating element for each reference electrode, in particular for the first reference electrode and the second reference electrode. For example, the heating element of the first reference electrode may have a different voltage applied to it than is applied to the heating element of the second reference electrode. The average temperature of the first reference electrode may, in particular, be increased relative to the average temperature of the second reference electrode in such a way that the internal resistance and/or the electrochemical performance of the first reference electrode and/or of the second reference electrode may thereby be influenced. The average temperature of the first reference electrode may, for example, be at least 10° C. higher than the average temperature of the second reference electrode, preferably at least 50° C. higher and more preferably at least 100° C. higher. The average temperature may, in particular, be a temperature integrated over the entire volume of the first reference electrode and/or of the second reference electrode, weighted with the volume of the first reference electrode and/or the volume of the second reference electrode.

A material composition of the first reference electrode may, for example, differ from a material composition of the second reference electrode. A material composition may in principle be understood as being a composition of the materials, in particular of the first reference electrode and/or the second reference electrode, for example a paste composition and/or a solid electrolyte composition and/or a bulk composition, for example of the components surrounding the first reference electrode and/or the second reference electrode. The material composition of the first reference electrode may preferably differ from the material composition of the second reference electrode in such a way that, as a result, the electrochemical performance of the first reference electrode is preferably higher relative to the second reference electrode and/or the first internal resistance is preferably lower relative to the second internal resistance.

A minimum distance between the first electrode and the first reference electrode may, for example, be smaller than a minimum distance between the first electrode and the second reference electrode. The minimum distance may preferably be the length of a path between the first electrode and the first reference electrode or the second reference electrode, the path preferably extending in each case in such a way that the internal resistance along that path is at a minimum between the first electrode and the first reference electrode or the second reference electrode. In particular, the minimum distance may, for example, be the distance that may be travelled by the gas and/or the gas component, for example oxygen ions, between the first electrode and the first reference electrode or the second reference electrode in the shortest time. Preferably, the average distance between the first electrode and the first reference electrode may be shorter by an extent such that, as a result, the electrochemical performance of the first reference electrode relative to the second reference electrode is preferably higher and/or the first internal resistance relative to the second internal resistance is preferably lower.

The second reference electrode may, for example, exhibit a poorer connection to the solid electrolyte than does the first reference electrode. The poorer connection may, in particular, take the form of a poor mechanical connection and/or chemical connection and/or electrical connection and/or electrochemical connection. Preferably, the connection of the second reference electrode to the solid electrolyte may be poorer than the connection of the first reference electrode to the solid electrolyte to an extent such that, as a result, the electrochemical performance of the first reference electrode relative to the second reference electrode is preferably higher and/or the first internal resistance relative to the second internal resistance is preferably lower.

The first reference electrode and the second reference electrode may have at least one common layer. For example, the first reference electrode and the second reference electrode may consist of one layer. The porosity of that layer and hence the gas diffusion in that layer should preferably be low.

The sensor device according to the present invention may preferably be a step-change probe, for example a planar step-change probe, in particular a step-change probe for pumped and unpumped operation. The sensor device may, in particular, include at least one $\lambda=1$-sensor, in particular at least one $\lambda=1$-sensor that may be selectively operated with a pumped reference or with an air reference.

In a further aspect of the present invention, a method for operating a sensor device, in particular a sensor device as described above, is described. In a first operating mode, for example an operating mode as described above, in particular in the operating mode with a pumped reference, a pump voltage and/or a pump current may be applied to the sensor element between the first electrode and the first reference electrode, while in the second operating mode, in particular in the operating mode with an air reference, the sensor element is operated without voltage and without pump current between the first electrode and the first reference electrode. In the first operating mode and/or in the second operating mode, the proportion of the gas component is deduced, in particular if the total pressure is known, and, for example, also the proportion of oxygen is deduced, by sensing of a voltage and/or an electric current between the first electrode and the first reference electrode and/or between the first electrode and the second reference electrode and/or between at least one electrical supply line of the first electrode and at least one electrical supply line of the first reference electrode and/or of the second reference electrode.

The sensor device according to an example embodiment of the present invention and the method according to an example embodiment of the present invention may have a great many advantages over conventional sensor devices and methods. For example, the example sensor device according to the present invention and the method according to the invention, in particular the example design according to the present invention, are able to offer the advantage that the sensor element, in particular the probe, is capable of being operated both with a pumped reference, for example in the first operating mode, and with an air reference, for example in the second operating mode. Consequently, the sensor element, in particular the probe, may be compatible, for example, with a large number of control devices and/or drives. In the first operating mode, for example in the case of operation with a pumped reference, an advantage that may be gained is that the second reference electrode is capable of acting as an "overpressure valve" in relation to the first reference electrode. In that manner it is possible, for example, to keep the oxygen partial pressure $p(O_2)$ constant, in particular in a gas region of the first reference electrode, in particular close to the first reference electrode, irrespective of the reference pump current, for example the pump current between the first electrode and the first reference electrode. In that manner it is possible, for example, to increase the accuracy of a characteristic curve, in particular compared with sensor devices and methods of the related art, and/or to obtain a high accuracy of a characteristic curve since the operating conditions may, for example, be kept more stable.

BRIEF DESCRIPTION OF THE DRAWINGS

Exemplary embodiments of the present invention are illustrated in the Figures and are described in detail below.

DETAILED DESCRIPTION OF EXAMPLE EMBODIMENTS

Figure 1:
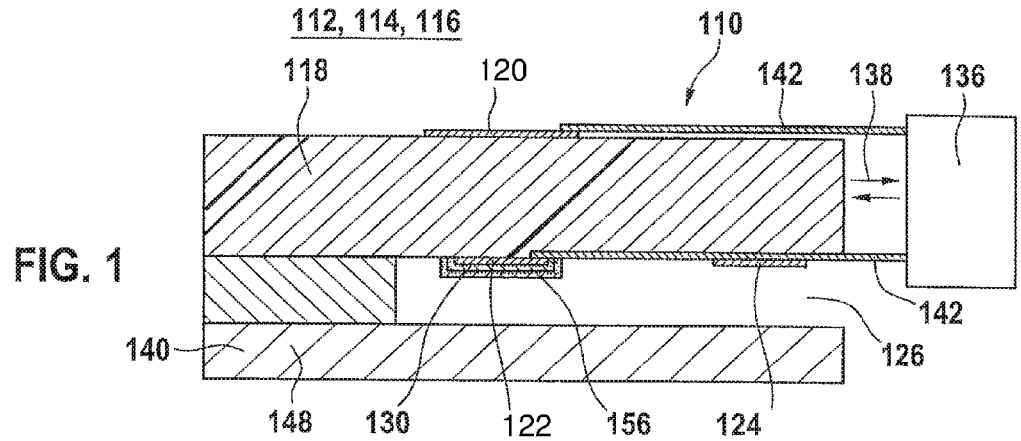
FIG. 1 shows a first exemplary embodiment of a sensor device according to the present invention.

FIGS. 1, 2, 4A and 4B, 5A and 5B show exemplary embodiments of an example sensor device 110 according to the present invention for sensing at least a proportion of at least one gas component, in particular oxygen, of a gas 112 in a measurement gas space 114, in particular for the detection of oxygen in an exhaust gas 116 of a combustion machine. Sensor device 110 includes at least one sensor element 118. Sensor element 118 includes at least one first electrode 120 and at least one first reference electrode 122 and at least one second reference electrode 124. Second reference electrode 124 and optionally also first reference electrode 122 are connected to at least one reference gas channel 126, in particular are connected, for example, in such a way that an exchange of the gas component, in particular a gas exchange, for example of oxygen ions, is able to take place. First electrode 120 is connected to first reference electrode 122 and to second reference electrode 124 by at least one respective solid electrolyte 128. Sensor element 118 has at least one diffusion element 130 between first reference electrode 122 and reference gas channel 126. Diffusion element 130 may, in particular, be a diffusion layer 156. By virtue of diffusion element 130, a gas exchange may be made possible between first reference electrode 122 and reference gas channel 126. The gas exchange may preferably take place exclusively through diffusion layer 156. In principle, diffusion element 130 and/or optionally diffusion layer 156 may also be sealed in a gas-tight manner, for example completely impermeably, with respect to reference gas channel 126, for example by at least one gas-tight covering. Thus, as an alternative to or in addition to diffusion layer 156, at least one cover element, for example, may be inserted, for example a completely gas-tight cover layer. For example, sensor element 118 may have at least one gas-tight covering between first reference electrode 122 and reference gas channel 126. An overpressure, in particular an oxygen overpressure, at first reference electrode 122 may, for example, be reduced by a conduction of oxygen ions to second reference electrode 124, for example with subsequent oxidation.

Reference gas channel 126 may preferably be of an open configuration. Sensor device 110 according to the present invention, in particular the design according to the present invention, may be based, in particular, on the reference gas channel 126, for example a reference air channel, being of an open configuration and/or on two reference electrodes, in particular first reference electrode 122 and second reference electrode 124, being implemented, it being possible for one of electrodes 135, in particular first reference electrode 122, to be covered by diffusion layer 156. Diffusion layer 156 preferably has a low porosity. Preferably, diffusion layer 156 has such a low porosity that no rich gas is able to diffuse from reference gas channel 126 to first reference electrode 122. However, the porosity should be so high that no oxygen overpressure is able to form, in particular at first reference electrode 122 and/or at second reference electrode 124, which could, for example, cause sensor element 118 to burst.

First reference electrode 122 and second reference electrode 124, in particular the reference electrodes, may preferably be electrically short-circuited, for example by common supply lines 142. Sensor element 118 may preferably have a first internal resistance (R1) 132 between first electrode 120 and first reference electrode 122. Sensor element 118 may preferably have a second internal resistance (R2) 134 between first electrode 120 and second reference electrode 124. First internal resistance 132 may preferably be smaller than second internal resistance 134. In particular, first internal resistance (R1) 132, preferably between first electrode 120, in particular an outer pumping electrode, and first reference electrode 122, may be low-resistance in comparison with second internal resistance (R2) 134, in particular between first electrode 120, for example the outer pumping electrode, and second reference electrode 124, as shown, for example, in FIG. 2. "Low-resistance" may preferably be understood here as meaning that a high ion-conductivity may exist.

An electrochemical performance of first reference electrode 122 may preferably be higher than an electrochemical performance of second reference electrode 124. For example, the reference electrodes, in particular first reference electrode 122 and second reference electrode 124, may be configured in such a way that second reference electrode 124, which may, for example, be in the form of an air reference electrode, has a lower electrochemical performance than first reference electrode 122, which may preferably be provided with a diffusion layer 156, for example with a diffusion element 130. A reduction in the electrochemical performance may be obtained, for example, through a different, in particular a higher, electrode temperature, especially a higher average temperature of first reference electrode 122, and/or through a different paste composition of electrode 135, for example of first reference electrode 122 in comparison with second reference electrode 124, and/or through a different geometry of electrode 135, for example of first reference electrode 122 in comparison with second reference electrode 124, as will be described, for example, in the following.

Sensor device 110 may include at least one drive 136. Drive 136 may, for example, be connected to sensor element 118 via an interface 138, as shown, for example, in FIG. 1, FIG. 2, FIG. 4A and FIG. 5A. Drive 136 may, however, also be completely or partially integrated in sensor element 118. Drive 136 may, for example, also be completely or partially integrated in other components, for example in a plug and/or in an engine control. Drive 136 may, for example, include at least one application device in order to apply current and/or voltage to electrodes 135, for example first electrode 120 and/or first reference electrode 122 and/or second reference electrode 124. The application device may, for example, be a voltage source and/or a current source. The application device may, in particular, include electrical lines. For example, the application device may include, in particular, at least two heating supply lines, in particular for supplying a heating element 140, in particular at least one heating film 148, with voltage and/or electric current. In addition, drive 136 may include, where applicable, at least one measuring device, for example at least one voltage-measuring device and/or at least one current-measuring device. In addition, drive 136 may optionally include, for example, at least one evaluation device, for example at least one data-processing device. Further optionally, drive 136 may include at least one signal generator. Drive 136 may optionally include, in addition, at least one closed-loop controller, for example at least one lock-in controller.

Drive 136 may, in particular, be configured in a first operating mode to apply to sensor element 118 a pump voltage and/or a pump current between first electrode 120, for example the outer electrode, and first reference electrode 122. In the first operating mode, in particular an operating mode with a pumped reference may be involved. Drive 136 may further be configured in a second operating mode to operate sensor element 118 without pump voltage and without pump current between first electrode 120, in particular an outer electrode, and first reference electrode 122. Drive 136 may further be configured, for example in the first operating mode and/or in the second operating mode, to deduce the proportion of the gas component, for example an oxygen partial pressure, by sensing of a voltage and/or an electric current between first electrode 120 and first reference electrode 122 and/or between first electrode 120 and second reference electrode 124 and/or between at least one electrical supply line 142 of first electrode 120 and at least one electrical supply line 142 of first reference electrode 122 and/or of second reference electrode 124. In the first operating mode, in particular in an operating mode with a pumped reference, it is possible, for example owing to the lower first internal resistance 132 in comparison with second internal resistance 134, to increase a local partial pressure, in particular an oxygen partial pressure $p(O_2)$, in diffusion element 130, in particular in diffusion layer 156, by virtue of the fact that a current, in particular an ion current, is able to flow preferentially between first electrode 120 and first reference electrode 122, in particular in comparison with a current from first electrode 120 to second reference electrode 124, in particular in which oxygen ions may be transported from first electrode 120 to first reference electrode 122. For example, in that manner it is possible to prevent CSD, in particular at first reference electrode 122. In the case of a difference in internal resistances, for example between first internal resistance 132 and second internal resistance 134, of, for example, $1000\Omega$ and a reference pump current of 50 μA between first electrode 120 and the reference electrodes, in particular first reference electrode 122 and second reference electrode 124, there is obtained, for example, a Nernst voltage of $1000\ \Omega \times 50\ \mu A = 50$ mV at first reference electrode 122, in particular an oxygen partial pressure at first reference electrode 122 that is higher than an oxygen partial pressure at second reference electrode 124 by a factor of 10. In that manner, first reference electrode 122, for example, should dominate the Nernst voltage, in particular owing to the lower first internal resistance 132 RiDC.

Figure 3:
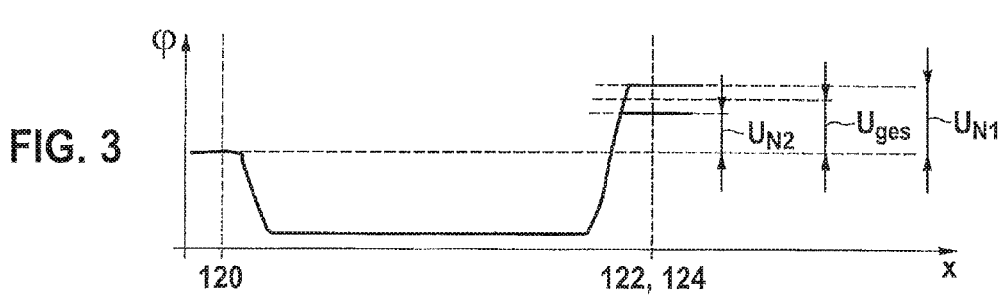
FIG. 3 shows an example of a potential variation between a first electrode and a first reference electrode and between the first electrode and a second reference electrode.

In particular, an electric mixed potential is able to form, preferably between first reference electrode 122 and second reference electrode 124. The electric mixed potential may be described, for example, by a total voltage of $U_{N1} \geq U_{total} \geq U_{N2}$. $U_{N1}$ may preferably be a Nernst voltage between first electrode 120, in particular the outer pumping electrode, and first reference electrode 122. $U_{N2}$ may preferably be a Nernst voltage between first electrode 120, in particular the outer pumping electrode, and second reference electrode 124. In that manner it is possible, for example, for an effect of a CSD at second reference electrode 124, if there is any, to be reduced. At first, in particular without compensating currents between first reference electrode 122 and second reference electrode 124, a potential variation as shown, for example, in FIG. 3, may be produced. FIG. 3 shows a potential variation φ as a function of a distance x, in particular as indicated by the vertical dashed lines, in particular a distance x between first electrode 120, in particular the outer pumping electrode, and a reference electrode in each case, in particular first reference electrode 122 and second reference electrode 124. FIG. 3 shows, in particular, a potential variation in the case where first electrode 120, in particular the outer pumping electrode, is exposed, for example, to a rich gas and second reference electrode 124 is suffering from slight CSD and no compensating currents are flowing between first reference electrode 122 and second reference electrode 124. The measured total voltage $U_{total}$ in particular a Nernst voltage, is preferably made up of the individual voltages at first reference electrode 122 and second reference electrode 124, as described above.

A partial pressure difference, in particular a $pO_2$ difference, occurring, for example, between first reference electrode 122 and second reference electrode 124, for example during the first operating mode, in particular in the case of a pumped reference, may, for example, cause a current, in particular an $O_2$ current, from first reference electrode 122 to second reference electrode 124, which current may be made possible, in particular, by the electronic short-circuit. Possible CSD at second reference electrode 124 may in that manner, for example, be at least partially reduced. Generally, however, it is not possible for CSD at second reference electrode 124 to be completely prevented in that manner. The current, for example a compensating current from first reference electrode 122 to second reference electrode 124, may, for example, be from 1 µA to 10 mA, preferably from 10 µA to 1 mA, more preferably approximately 100 µA. A limiting current of the reference channel, in particular of the open reference channel, may, for example, be from 5 µA to 50 mA, for example from 50 µA to 5 mA, more preferably approximately 500 µA. Therefore, the current, in particular the compensating current, between first reference electrode 122 and second reference electrode 124, does not as a rule deal with the limiting current of the open reference channel.

In the second operating mode, in particular in the case of an air reference, a possible CSD, for example at first reference electrode 122, may preferably be reduced and/or prevented by a current, in particular by an $O_2$ current, from second reference electrode 124 to first reference electrode 122. In the second operating mode, in particular in the case of an air reference, as a rule no reference pump current flows, as a result of which, for example, a voltage drop over an internal resistance difference may become 0 or may generally be determined only by the compensating current. Therefore, the compensating current decays preferably exponentially and as a rule a complete equalization of the partial pressures, in particular the oxygen partial pressures, occurs with a delay. The compensating current may usually be determined by the difference of the oxygen partial pressures at first reference electrode 122 and second reference electrode 124 and by the internal resistance between the two, in particular the internal resistance between first reference electrode 122 and second reference electrode 124.

Sensor element 118, in particular the probe, may be selectively operated in the first operating mode, with a pumped reference, or in the second operating mode, with an air reference, preferably thereby determining and/or regulating whether or that an electric current and/or a voltage is applied between first electrode 120 and first reference electrode 122, as is required, for example, in the first operating mode.

The principle of operation may, in particular, be based on first internal resistance 132 of sensor element 118, for example between first electrode 120, in particular the outer pumping electrode, and second reference electrode 124, being increased in comparison with second internal resistance 134, for example between first electrode 120, in particular the outer pumping electrode, and first reference electrode 122. The difference between first internal resistance 132 and second internal resistance 134 may be obtained through different embodiments of sensor device 110, as will be described, for example, in the following and as shown by way of example in FIGS. 1, 2 4A and 4B, 5A and 5B.

First reference electrode 122 may, in particular, be covered with a porous material, in particular with a porous diffusion element 130. In particular, first reference electrode 122 may be a reference electrode covered with a porous diffusion element 130 as shown, for example, in FIG. 1. In particular, in the case of the first exemplary embodiment, which is illustrated in FIG. 1 and FIG. 2, first reference electrode 122 is constructed to be separate from second reference electrode 124, the two reference electrodes, for example first reference electrode 122 and second reference electrode 124, having a common supply line 142, in particular an electrical supply line 142, so that first reference electrode 122 is preferably short-circuited with second reference electrode 124.

Figure 2:
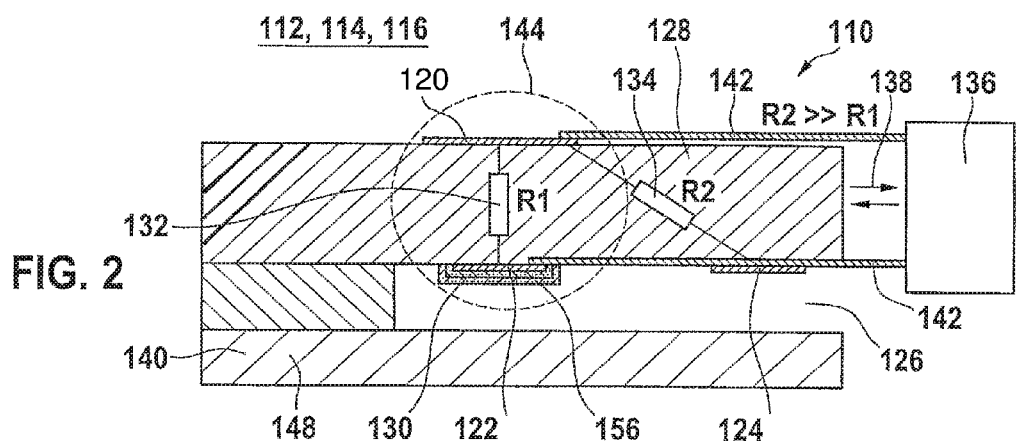
FIG. 2 shows a schematic illustration of internal resistances of the first exemplary embodiment of an example sensor device according to the present invention.
Figure 4A:
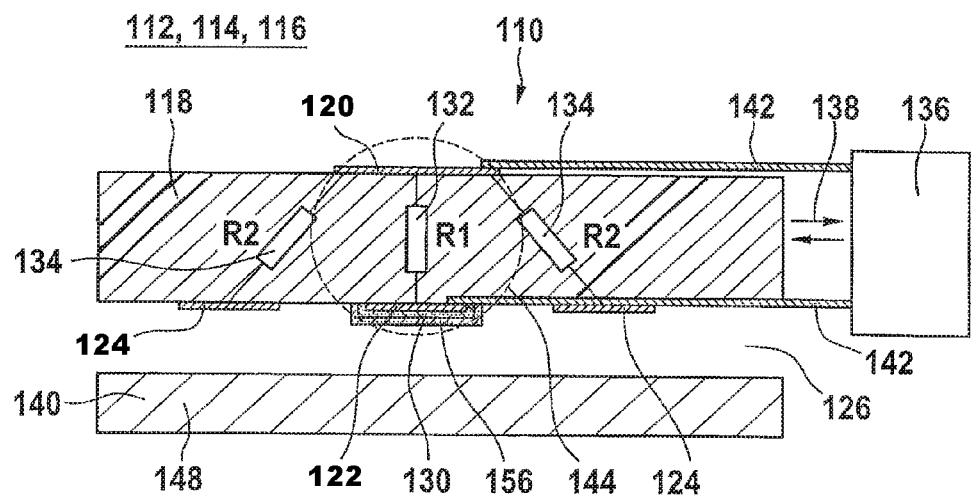
FIG. 4A shows a schematic illustration of a second exemplary embodiment of an example sensor device according to the present invention, with internal resistances illustrated schematically.
Figure 4B:
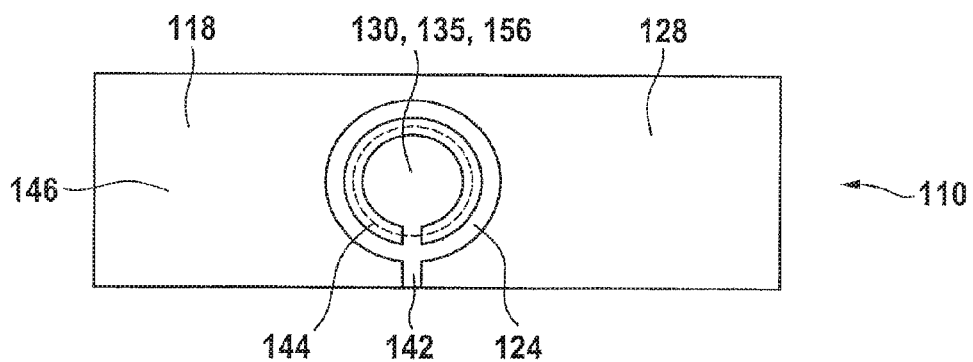
FIG. 4B shows a plan view of a sensor film of the second exemplary embodiment of a sensor device according to the present invention.
Figure 5A:
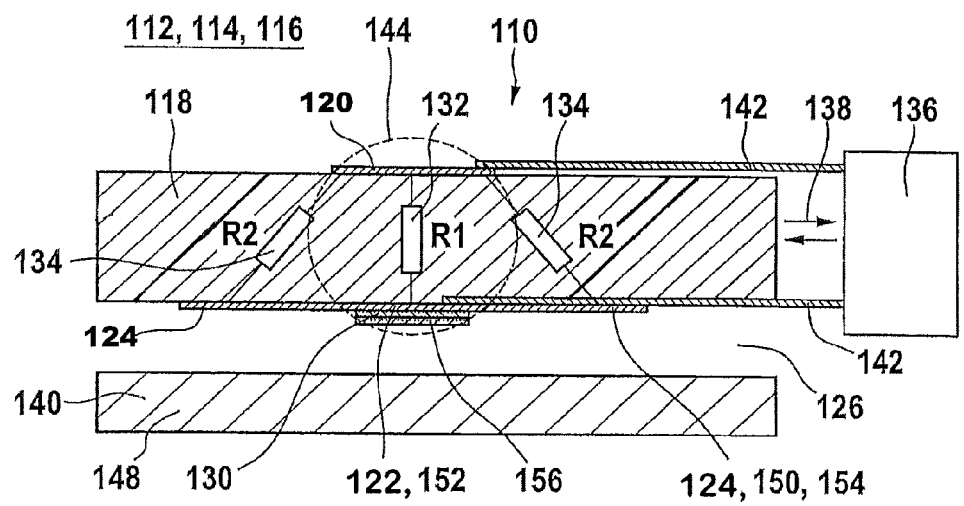
FIG. 5A shows a schematic illustration of a third exemplary embodiment of a sensor device according to the present invention, with internal resistances illustrated schematically.

Second reference electrode 124 may, for example, be a withdrawn first reference electrode 122, in particular a first reference electrode 122 that may be disposed outside of a hot spot 144, as illustrated, for example, in FIG. 2, FIG. 4A and FIG. 5A. A hot spot 144 may preferably be a region of sensor element 118 that has a higher temperature, for example a higher average temperature, than another part of sensor element 118. Hot spot 144 is indicated schematically in FIG. 2, FIG. 4A and FIG. 5A by a circle in each case. Sensor element 118 may preferably have at least one hot spot 144. Hot spot 144 may, for example, have a higher average temperature by being, for example, heated, for example by heating element 140, for example by hot spot 144 being in proximity to heating element 140. An average temperature of first reference electrode 122 may, for example, be higher than an average temperature of second reference electrode 124. For example, second reference electrode 124 may be positioned outside of hot spot 144, for example in the direction toward supply lines 142, for example of connection contacts, and/or first reference electrode 122 may preferably be disposed at least partially in hot spot 144. Hot spot 144 may, for example, be of an approximately circular configuration, as illustrated in particular in FIGS. 2, 4A, 4B, 5A and 5B. In principle, hot spot 144 may be of any shape, in particular may have any extent, for example may be elliptical or have another round shape; in particular, hot spot 144 may also have a three-dimensional extent, for example may be approximately spherical or ellipsoidal. By positioning second reference electrode 124 in the direction toward supply line 142 it is also possible, for example, to extend a geometric spacing between first electrode 120, for example an outer pumping electrode, and second reference electrode 124, in particular in comparison with a geometric spacing between first electrode 120 and first reference electrode 122, as a result of which, for example, second internal resistance 134 may increase relative to first internal resistance 132.

In particular, a minimum distance between first electrode 120 and first reference electrode 122 may be smaller than a minimum distance between first electrode 120 and second reference electrode 124, which likewise may reduce first internal resistance 132 relative to second internal resistance 134.

The internal resistance, in particular first internal resistance 132, may, in particular, also be reduced relative to second internal resistance 134 by a lower average temperature, for example by a lower operating temperature, whereby, for example, a high-resistance connection of second reference electrode 124 may be achieved. Arrangement of first reference electrode 122 in hot spot 144, which may be generally accompanied by an increased average temperature of first reference electrode 122, may in that manner lead, in particular, to a lower first internal resistance 132, in contrast to a second internal resistance 134 of second reference electrode 124 which may preferably be disposed outside of hot spot 144.

In a second exemplary embodiment, as illustrated in FIGS. 4A and 4B, second reference electrode 124 may surround first reference electrode 122 preferably in the shape of a ring. For example, second reference electrode 124 may be of a ring-shaped configuration and/or may be disposed at least partially, and preferably completely, outside of hot spot 144. In the second exemplary embodiment also, as illustrated in FIG. 4A and FIG. 4B, second reference electrode 124 may preferably be positioned outside of hot spot 144. In that manner, an electrochemical activity, for example, of second reference electrode 124 may be lowered relative to first reference electrode 122, for example combined with an increase in second internal resistance 134 compared with first internal resistance 132. An advantage of the second exemplary embodiment as illustrated in FIGS. 4A and 4B and/or of a ring-shaped second reference electrode 124 may, in particular, be the symmetry, since, for example, with a symmetry it is possible to avoid mechanical stresses in sensor element 118, for example following a sintering process.

Figure 5B:
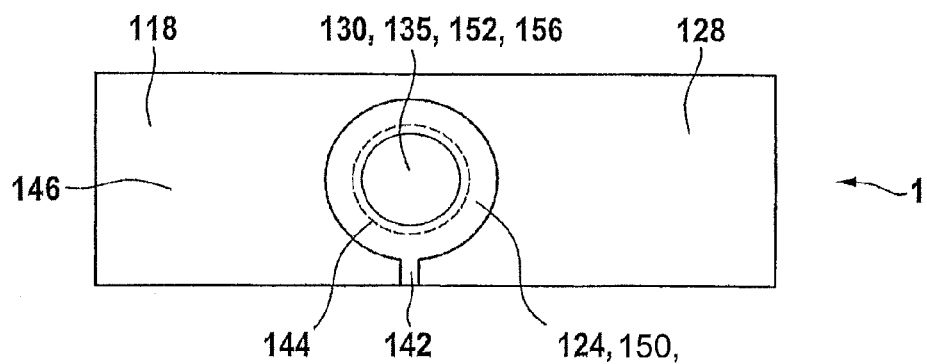
FIG. 5B shows a plan view of a sensor film of the third exemplary embodiment of an example sensor device according to the present invention.

FIGS. 4B and 5B each show a plan view of sensor elements 118, in particular of sensor films 246, of exemplary embodiments of sensor devices 110 according to the present invention. In particular, FIGS. 4B and 5B show at least one sensor film 146, FIGS. 1, 4A and 5A show the at least one heating film 148. Sensor film 146 may preferably be a component, especially a layer, of sensor element 118, which, for example, encompasses solid electrolyte 128. Heating film 148 may preferably be a component, especially a layer, of sensor element 118, which, for example, encompasses the heating element. FIGS. 1, 4A, 5A show, in particular, cross-sections of exemplary embodiments of sensor devices 110 according to the invention, in particular of sensor elements 118.

FIGS. 5A and 5B show by way of example a third exemplary embodiment of a sensor device 110 according to the present invention, wherein first reference electrode 122 and second reference electrode 124 may be of a combined configuration. For example, first reference electrode 122 and second reference electrode 124 may have at least one common layer 150. For example, during fabrication of sensor device 110 according to the present invention, first reference electrode 122 and second reference electrode 124 may be printed contiguously. The region that may be assigned to first reference electrode 122, for example at least a first region 152, may in addition be covered by a diffusive layer, for example by a diffusion element 130. For example, first reference electrode 122 and second reference electrode 124 may be implemented by a thick single electrode 135, preferably with a high-resistance support structure. Thick single electrode 135 may, for example, be heated solely by the contact with the zirconium dioxide ($ZrO_2$), for example on a heater side of an open reference channel, for example a reference gas channel 126. In that manner it is possible to implement, for example, first reference electrode 122, in particular a diffusion-protected first reference electrode 122, and/or the hotter first reference electrode 122. In this exemplary embodiment, sensor element 118 may preferably include at least one combined electrode 135, in particular an electrode 135 that includes first reference electrode 122 and second reference electrode 124 in combination, it being possible for there to be preferably at least one diffusion layer 156 over first reference electrode 122.

In the second exemplary embodiment and in the third exemplary embodiment, it is possible, in particular, for at least two second internal resistances 134, for example as shown in FIGS. 4A and 5A, to be present and/or to be schematically illustrated, in particular owing to the ring-shaped second reference electrode 124.

First reference electrode 122 may, in particular, be formed by the at least one first region 152, preferably at least partially covered by diffusion element 130, of an electrode 135 disposed in reference gas channel 126. Second reference electrode 124 may be formed by at least one second region 154 of electrode 135 disposed in reference gas channel 126. First region 152 and second region 154 may preferably be different and first region 152 may be covered by at least one diffusion layer 156 toward reference gas channel 126. Diffusion layer 156 may form at least a part of diffusion element 130. For example, a geometry of first reference electrode 122 may furthermore differ from a geometry of second reference electrode 124.

For example, a material composition of first reference electrode 122 may differ from a material composition of second reference electrode 124. In particular, different electrode configurations may be present, for example different configurations of first reference electrode 122 and/or of second reference electrode 124, for example as described above, preferably in order to make second internal resistance 134 higher than first internal resistance 132. In particular, first reference electrode 122 may be implemented differently from second reference electrode 124, in particular by a different electrode configuration and/or a different electrode geometry and/or a different material composition, in order likewise to increase second internal resistance 134 relative to first internal resistance 132. Preferably, the alteration, in particular a dissimilarity, may be such that the electrochemical activity of second reference electrode 124 is reduced relative to the electrochemical activity of first reference electrode 122. In that manner, it is also possible, in particular, for second internal resistance 134 to increase relative to first internal resistance 132. The alteration and/or the different electrode configuration and/or the reduction of the electrochemical activity of second reference electrode 124 and/or the increasing of second internal resistance 134 relative to first internal resistance 132 may furthermore be effected, for example, by a measure selected from a group consisting of: variation of the content of a support structure of an electrode paste, in particular of the first reference electrode 122 and/or of the second reference electrode 124; a paste additive that is preferably not electrochemically active, for example in the case of second reference electrode 124, for example $Al_2O_3$; a reduced electrode surface area, in particular of second reference electrode 124; a poor electrode connection, in particular of second reference electrode 124, to a film, in particular to sensor film 146, for example to solid electrolyte 128; an altered porosity of first reference electrode 122 and/or of second reference electrode 124, in particular a porosity of first reference electrode 122 that may lead to a lengthening of a three-phase boundary relative to second reference electrode 124, the three-phase boundary usually being one where an electronic phase and an ionic phase and a gaseous phase adjoin one another; an altered thickness of first reference electrode 122 and/or of second reference electrode 124, in particular an increase in the thickness of first reference electrode 122 relative to second reference electrode 124; an altered percolation of the electronic phase, in particular a coherent electronically conductive material, for example of Pt, and/or of the ionic phase, for example $ZrO_2$, of first reference electrode 122 and/or of second reference electrode 124, especially preferably of first reference electrode 122 relative to second reference electrode 124; by a change in the electrochemically active paste content, for example of first reference electrode 122 and/or of second reference electrode 124, preferably of first reference electrode 122 relative to second reference electrode 124, for example by complete or partial replacement of Pt by Pd. In particular, second reference electrode 124 may preferably have a poorer connection to solid electrolyte 128 than does first reference electrode 122.

In addition, properties of the printed solid electrolyte 128 may differ, preferably in order to increase second internal resistance 134 relative to first internal resistance 132. For example, the resistance ratios between first internal resistance 132 and second internal resistance 134 may be adjusted by modification of a printed solid electrolyte material itself, in particular in contrast to a modification of the electrode pastes, in particular the pastes of first reference electrode 122 and/or of second reference electrode 124. For example, a solid electrolyte film, in particular a film, for example sensor film 146, that may preferably at least partially form solid electrolyte 128, may be configured in such a way, for example by inlay technology, that the solid electrolyte film preferably has regions with higher ion conductivity and regions with lower ion conductivity. For example, first region 152 may preferably have high ion conductivity and/or second region 154 may preferably have low ion conductivity. Preferably, in that case second reference electrode 124 is printed, for example, onto a region of low conductivity, for example second region 154, in particular of lower ion conductivity, and/or first reference electrode 122 and/or an outer electrode is printed onto a region, in particular first region 152, of higher conductivity, in particular higher ion conductivity.

In addition, a temperature, for example, in particular a temperature and/or an average temperature of at least one portion of sensor element 118, may be reduced, for example by regulating a heating element 140, a reduction in the temperature of at least one portion of sensor element 118 being able to produce, for example, a reduction in the catalytic activity of at least one portion of sensor element 118, a reduction in the catalytic activity of at least one portion of sensor element 118, for example of first reference electrode 122 and/or of second reference electrode 124, being able to produce a reduction in the CSD.

For example, first reference electrode 122 may be provided with Au and may thus become a HC sensor, for example at a lower temperature of at least one portion of sensor element 118, for example 200 to 1000° C., in particular 500 to 800° C., preferably 500° C. In that manner it is possible, for example, for HC oxidation in the reference, for example at first reference electrode 122 and/or at second reference electrode 124, to be avoided, in particular avoided in general, while at the same time an evaluation of the oxygen partial pressure, in particular the $O_2$ partial pressure, may nevertheless be possible since, for example, with sufficiently high-resistance tapping of the probe signal, the electrode function, for example the function of first electrode 120 and/or the function of first reference electrode 122 and/or the function of second reference electrode 124, seldom and preferably never requires a pump-loading of a reference electrode, for example first reference electrode 122 and/or second reference electrode 124, in relation to the outer pumping electrode, for example first electrode 120. In that manner, for example, a required extraction of oxygen at the reference electrode, for example first reference electrode 122 and/or second reference electrode 124, may continue to be possible unhindered. This may reduce, for example, a risk of hydrocarbons (HC) diffusing in from an oxygen consumption by oxidation to purely a displacement of the oxygen, for example similarly to the case of water.

What is claimed is:

1. A sensor device for sensing at least a proportion of at least one gas component of a gas in a measurement gas space, comprising:
at least one sensor element including at least one first electrode, at least one first reference electrode, and at least one second reference electrode, wherein the second reference electrode is connected to at least one reference gas channel, the first electrode is connected to the first reference electrode and the second reference electrode by at least one respective solid electrolyte, the sensor element further includes at least one diffusion element which is connected to the first reference electrode and which at least partially surrounds the first reference electrode.

2. The sensor device as recited in claim 1, wherein the diffusion element is at least partially disposed between the first reference electrode and the reference gas channel.

3. The sensor device as recited in claim 1, wherein the first reference electrode is connected to the reference gas channel, a gas exchange between the first reference electrode and the reference gas channel through the diffusion element being made possible by the diffusion element.

4. The sensor device as recited in claim 1, wherein the first reference electrode is sealed with respect to the reference gas channel, a direct gas exchange between the first reference electrode and the reference gas channel being prevented.

5. The sensor device as recited in claim 1, wherein the sensor element has a first internal resistance between the first electrode and the first reference electrode, wherein the sensor element has a second internal resistance between the first electrode and the second reference electrode, and wherein the first internal resistance is smaller than the second internal resistance.

6. The sensor device as recited in claim 1, wherein the first reference electrode and the second reference electrode are electrically short-circuited.

7. The sensor device as recited in claim 1, wherein the first reference electrode is formed by at least one first region of an electrode disposed in the reference gas channel, wherein the second reference electrode is formed by at least one second region of the electrode disposed in the reference gas channel, and wherein the first region and the second region are different and wherein the first region is covered toward the reference gas channel by at least one diffusion layer, the diffusion layer forming at least a part of the diffusion element.

8. The sensor device as recited in claim 1, wherein the reference gas channel is of an open configuration.

9. The sensor device as recited in claim 1, wherein the sensor device includes at least one drive, the drive being configured to apply to the sensor element, in a first operating mode, at least one of a pump voltage and a pump current, between the first electrode and the first reference electrode, the drive being further configured to operate the sensor element in a second operating mode without pump voltage and without pump current between the first electrode and the first reference electrode, the drive being further configured to deduce in at least one of the first operating mode and the second operation mode a proportion of the gas component by sensing of at least one of a voltage and an electric current, at least one of: i) between the first electrode and the first reference electrode, ii) between the first electrode and the second reference electrode, and iii) between at least one electrical supply line of the first electrode and at least one electrical supply line of at least one of the first reference electrode and of the second reference electrode.

10. The sensor device as recited in claim 1, wherein a geometry of the first reference electrode differs from a geometry of the second reference electrode.

11. A sensor device for sensing at least a proportion of at least one gas component of a gas in a measurement gas space, comprising:
at least one sensor element including at least one first electrode, at least one first reference electrode, and at least one second reference electrode, wherein the second reference electrode is connected to at least one reference gas channel, the first electrode is connected to the first reference electrode and the second reference electrode by at least one respective solid electrolyte, the sensor element further includes at least one diffusion element which is connected to the first reference electrode, wherein the sensor device is for detecting oxygen in an exhaust gas of a combustion machine.

12. A method for operating a sensor device that senses at least a proportion of at least one gas component of a gas in a measurement gas space, the sensor device including at least one sensor element having at least one first electrode, at least one first reference electrode, and at least one second reference electrode, wherein the second reference electrode is connected to at least one reference gas channel, the first electrode is connected to the first reference electrode and the second reference electrode by at least one respective solid electrolyte, the sensor element further having at least one diffusion element which is connected to the first reference electrode, the method comprising:

applying, in a first operating mode, at least one of a pump voltage and a pump current, to the sensor element between the first electrode and the first reference electrode; and operating the sensor element, in a second operating mode, without pump voltage and without pump current between the first electrode and the first reference electrode;

wherein in at least one of the first operating mode and in the second operating mode, the proportion of the gas component is deduced by sensing of at least one of a voltage and an electric current, at least one of: i) between the first electrode and the first reference electrode, ii) between the first electrode and the second reference electrode, and iii) between at least one electrical supply line of the first electrode and at least one electrical supply line of at least one of the first reference electrode and of the second reference electrode.

* * * * *